United States Patent
Kelly et al.

(10) Patent No.: US 10,772,554 B2
(45) Date of Patent: Sep. 15, 2020

(54) METHODS AND SYSTEMS FOR THE DETECTION OF DISEASE

(71) Applicant: Joseph Michael Lawless Kelly, Duxbury, MA (US)

(72) Inventors: Joseph Michael Lawless Kelly, Duxbury, MA (US); Joseph Michael Kelly, Duxbury, MA (US)

( * ) Notice: Subject to any disclaimer, the term of this patent is extended or adjusted under 35 U.S.C. 154(b) by 777 days.

(21) Appl. No.: 14/916,754

(22) PCT Filed: Sep. 4, 2014

(86) PCT No.: PCT/US2014/054166
§ 371 (c)(1),
(2) Date: Jun. 30, 2016

(87) PCT Pub. No.: WO2015/057315
PCT Pub. Date: Apr. 23, 2015

(65) Prior Publication Data
US 2016/0192873 A1 Jul. 7, 2016

Related U.S. Application Data

(60) Provisional application No. 61/898,465, filed on Oct. 31, 2013, provisional application No. 61/873,822, filed on Sep. 4, 2013.

(51) Int. Cl.
*A61B 5/00* (2006.01)
*A61B 3/11* (2006.01)
(Continued)

(52) U.S. Cl.
CPC .......... *A61B 5/4064* (2013.01); *A61B 3/0025* (2013.01); *A61B 3/112* (2013.01);
(Continued)

(58) Field of Classification Search
CPC ... A61B 5/4064; A61B 5/4866; A61B 3/0025; A61B 3/112; A61B 3/14; A61B 5/4088;
(Continued)

(56) References Cited

U.S. PATENT DOCUMENTS 9,269,046 B2   2/2016  Rothman
9,433,354 B2   9/2016  Zelinsky
(Continued)

OTHER PUBLICATIONS

Giza et al. "The Neurometabolic Cascade of Concussion." Journal of Athletic Training. Journal of Athletic Training, 36(3), 2001, pp. 228-235 (Year: 2001).*

(Continued)

*Primary Examiner* — Jon Chang

(57) ABSTRACT

Disclosed herein are systems and methods for the detection of alterations in glucose metabolism in a subject. The disclosed methods and systems provide, in certain embodiments, administering a first eye test to the subject when the subject is in a normal state, obtaining a first set of one or more images of the first eye test of the subject, administering a second eye test to the subject and obtaining a second set of one or more images of the second eye test of the subject. The methods further provide for analyzing one or more differences identified between the first set of one or more images and the second set of one or more images.

20 Claims, 2 Drawing Sheets

(51) Int. Cl.
*A61B 3/14* (2006.01)
*A61B 3/02* (2006.01)
*A61B 3/113* (2006.01)
*A61B 3/00* (2006.01)

(52) U.S. Cl.
CPC .............. *A61B 3/113* (2013.01); *A61B 3/14* (2013.01); *A61B 3/145* (2013.01); *A61B 5/00* (2013.01); *A61B 5/4088* (2013.01); *A61B 5/4866* (2013.01)

(58) Field of Classification Search
CPC ........... A61B 3/145; A61B 5/00; A61B 3/113; A61B 3/02; G06T 2207/30041
See application file for complete search history.

(56) References Cited

U.S. PATENT DOCUMENTS

| | | | |
|---|---|---|---|
| 9,460,604 B1* | 10/2016 | Daniel | G08B 21/18 |
| 9,798,148 B2 | 10/2017 | Border | |
| 9,811,152 B2 | 11/2017 | Nortrup | |
| 10,022,049 B2 | 7/2018 | Klin | |
| 10,092,195 B2 | 10/2018 | Lovoi | |
| 10,338,091 B2 | 7/2019 | Wackym | |
| 2002/0099305 A1* | 7/2002 | Fukushima | A61B 3/112 600/558 |
| 2013/0278899 A1* | 10/2013 | Waldorf | A61B 3/032 351/209 |
| 2016/0022137 A1* | 1/2016 | Wetzel | A61B 5/1103 600/558 |

OTHER PUBLICATIONS

Watson et al. "The Role of Insulin Resistance in the Pathogenesis of Alzheimer's Disease: Implications for Treatment." CNS Drugs, vo. 17, issue 1, Jan. 2003, pp. 27-45 (Year: 2003).*

Ishii et al. "Construction of the Measurement System and its Experimental Study for Diagnosing Cerebral Functional Disorders Using Eye-Sensing HMD." Proceedings of the 41st SICE Annual Conference, Aug. 5, 2002, pp. 1248-1253 (Year: 2002).*

* cited by examiner

METHODS AND SYSTEMS FOR THE DETECTION OF DISEASE

FIELD OF THE INVENTION

The methods and systems disclosed herein relate to medicine and healthcare.

BACKGROUND

The human brain is highly sensitive to perturbations in oxygen and blood glucose levels. Cerebral hypoxia (i.e., reduced oxygen to the brain) is marked by uncontrolled movement, inability to focus, and changes in behavior. Changes in blood glucose levels are also marked by alterations in cognition. For instance, hypoglycemia can lead to function brain failure, which includes changes in behavior and coma (Philip Cryer. (2007) *J Clin Invest.* 117(4):868-870). Hyperglycemia, on the other hand, has been associated with slowing of all cognitive performance tests and an increased number of mental subtraction errors (Cox et al. (2005) *Diabetes Care.* 28(1):71-77).

There are many events that can lead to alterations in blood glucose and/or oxygen levels in the brain. These conditions include diabetes type 1 and type 2, hepatitis, kidney disease, medications, and endocrine deficiencies. Concussions are also an example of an event that can cause both localized and systemic alterations in oxygen and glucose levels in the brain. There are approximately four to five million concussions in the United States each year (Iverson et al. (2004) *Brain Injury.* 18(5):433-43). Many of these concussions occur in contact sports such as American football and ice hockey. Nevertheless, concussions have been identified in other sports such as baseball, soccer, and basketball. Concussions have also been a source of concern in the armed forces as well. Concussions, therefore, are a health risk for almost all athletes—both professional and amateur and soldiers.

At present, there are several methods of detecting a concussion in an individual. One method is a medical examination performed immediately after the concussion occurs. This methodology requires a medical professional to administer an examination to an individual—taking account of the individual's mental faculties as well as the individual's response to certain stimuli. In addition, the medical professional may utilize CT scans to identify brain damage if the individual appears to have a concussion. Other methods of detecting concussions include Post-Concussion Symptom Scale (PCSS), Balance Error Scoring System (BESS), and the five subscales of the Immediate Post-Concussion Assessment and Cognitive Testing (ImPACT). The most prevalent of these tests is the ImPACT testing regimen.

However, these detection methodologies have substantial drawbacks when an athlete, soldier, or other individual suffers a potential concussion in the field and requires immediate and reliable information. The medical examination lacks reliability due to the subjectivity of the examination and can take a significant amount of time to perform. When performing the examination, the medical professional is left to determine whether the individual suffered a concussion without any prior information regarding the subject's history. Regarding the CT scan, the device is not readily available outside of medical facilities.

The other methods lack reliability or reproducibility. A study of these methods established that "there is poor concurrent validity among three commonly used concussion tests and there is no baseline score that predicts whether post-concussion syndrome will occur" (Barlow et al. (2011) *Int J Sports Phys Ther.* 6(4):361-371). In other words, the validity of the most commonly used tests for concussions has not been established.

SUMMARY

Disclosed herein are methods and systems for the rapid, reliable, and objective detection of diseases in subjects. The disclosed methods and systems allow for clinicians to detect diseases utilizing changes in eye function and morphology caused by perturbations in glucose and/or oxygen levels in the brain of a subject. In certain instances, the methods and systems detect concussions. The disclosed methods and systems also allow for clinicians and other medical personnel to detect concussions close in time to when the concussion first occurs. In addition, medical personnel using the disclosed methods and systems would have a test that would allow for a more objective determination of the existence of a disease such as a concussion. A further advantage of the disclosed methods and systems is the ability of medical personnel to view the results of a test for a disease and compare the results to a baseline reading of the subject or alternatively to the results of a group of subjects of similar age and gender.

An aspect of the disclosed methods involves detecting a disease of a subject. In certain embodiments, the disease is associated with hypoglycemia. Exemplary diseases include hepatitis, diabetes type 1 and type 2, diseases of the kidney, insulinoma, nesidioblastosis, Addison's disease, under-active pituitary gland, mild traumatic brain injury such as concussion, and liver disease. In certain embodiments, the disease is a concussion. In particular embodiments, the disease is associated with hyperglycemia. Exemplary diseases associated with hyperglycemia include diabetes type 1 and type 2, stroke, myocardial infarction, dysfunction of the thyroid, dysfunction of the adrenal or pituitary gland, pancreatic cancer, infections, encephalitis, brain tumors, and meningitis. In additional embodiments, the methods detect hyperglycemia caused by medications such as corticosteroids, octreotide, beta blockers, epinephrine, thiazide diuretics, niacin, pentamidine, protease inhibitors, and L-asparaginase.

In certain embodiments, the methods identify a brain that has entered an insulin resistant state. Insulin resistance is a common factor in the development of Type 2 Diabetes (see, e.g., Chui et al. (2007) *Diabetes Res Clin Pract.* 77(2):237-244). Insulin resistance develops because cells in a tissue become insensitive to insulin or utilize insulin less efficiently. As insulin resistance becomes more acute, the level of insulin and blood glucose increase (see id.). Insulin resistance symptoms include high blood sugar, intestinal bloating, and brain fogginess and inability to focus. Studies have established that insulin resistance in the brain "precedes and contributes to cognitive decline" beyond the decline associated with diseases such as Alzheimer's disease" (see News Release, *Brain Insulin Resistance Contributes to Cognitive Decline in Alzheimer's Disease.* Perelman School of Medicine at the University of Pennsylvania Health System, Mar. 23, 2012).

Insulin resistance in the brain can be caused by many factors such as increased levels of insulin in the blood. In addition, insulin resistance can be caused by consumption of sugary drinks such as sodas and sports drinks (see Yoshida et al. (2007) *J Nutr.* 137(9):2121-2127). Without being held to any particular theory, it appears that consumption of sports drinks and high sugar diets sensitizes individuals to the effects of particular cognitive impairments such as mild traumatic brain injury and Alzheimer's disease. Insulin resistance can prolong the effects of cognitive impairments as well. Furthermore, an individual that suffers the effects of a concussion can have these effects last for longer periods of time due to insulin resistance and such individuals can be sensitized to further concussions.

In particular embodiments, the methods comprise administering a first eye movement test to the subject when the subject is in a normal state and obtaining a first image of the first eye movement test of the subject. In certain embodiments, the first image is a still image of the eye. In particular embodiments, the first image of the first eye movement test is a series of still images of the eye. In other embodiments, the first image is a moving visual image of the eye. The methods further comprise administering a second eye movement test to the subject and obtaining a second image of the second eye movement test of the subject. In certain embodiments, the second image is a still image of the eye. In particular embodiments, the second image of the second eye movement test is a series of still images of the eye. In other embodiments, the second image is a moving visual image of the eye.

In certain embodiments, the methods comprise analyzing a difference between the first image and the second image and detecting a disease such as a concussion when the second eye movement of the subject is altered compared to the first eye movement of the subject.

In some embodiments, a disease such as a concussion is detected when the eye movement of the subject in the second eye movement test is retarded as compared to the eye movement of the subject in the first eye movement test. In other embodiments, the first and the second eye movement tests are a King-Devick Test. In certain embodiments, the methods further comprise storing the first moving visual image of the first eye movement test of the subject in a storage medium.

In certain embodiments, the second eye movement test is administered after the subject has performed physical activity. In other embodiments, the second eye movement test is administered after the subject has sustained contact to the head. In still other embodiments, the second moving visual image is obtained within 30 minutes of the subject receiving a head trauma.

In particular embodiments, the methods further comprise storing the second image (such as a still image of the eye, a series of still images of the eye and/or a moving visual image of the eye) of the second eye movement test of the subject in a storage medium. In certain embodiments, the first and second eye movements are selected from the groups consisting of lateral eye movements, vertical eye movements, diagonal eye movements, dilation of a pupil, and combinations thereof. In other embodiments, a disease is detected when a second dilation of a pupil shown in the second image is altered when compared to a first dilation of the pupil shown in the first image. In still other embodiments, a disease is detected when a second lateral eye movement shown in the second image is altered when compared to a first lateral eye movement test shown in the first image.

In certain embodiments, a disease is detected when a second vertical eye movement shown in the second image is altered when compared to a first vertical eye movement test shown in the first image.

Another aspect of the disclosed methods involves detecting a disease of a subject by identifying an alteration in a structure of the eye. In certain embodiments, the disease is associated with hypoglycemia. Exemplary diseases include hepatitis, diabetes type 1 and type 2, diseases of the kidney, insulinoma, nesidioblastosis, Addison's disease, under-active pituitary gland, mild traumatic brain injury such as concussion, and liver disease. In certain embodiments, the disease is a concussion. In particular embodiments, the disease is associated with hyperglycemia. Exemplary diseases associated with hyperglycemia include diabetes type 1 and type 2, stroke, myocardial infarction, dysfunction of the thyroid, dysfunction of the adrenal or pituitary gland, pancreatic cancer, infections, encephalitis, brain tumors, and meningitis. In additional embodiments, the methods detect hyperglycemia caused by medications such as corticosteroids, octreotide, beta blockers, epinephrine, thiazide diuretics, niacin, pentamidine, protease inhibitors, and L-asparaginase.

In particular embodiments, the methods comprise administering a first eye test to the subject when the subject is in a normal state and obtaining a first image of the first eye test of the subject. In certain embodiments, the first image is a still image of the eye. In particular embodiments, the first image of the first eye test is a series of still images of the eye. The methods further comprise administering a second eye test to the subject and obtaining a second image of the second eye test of the subject. In certain embodiments, the second image is a still image of the eye. In particular embodiments, the second image of the second eye test is a series of still images of the eye.

In certain embodiments, the methods comprise analyzing a difference between the first image and the second image and detecting a disease such as a concussion when the second eye test of the subject is altered compared to the first eye test of the subject.

In some embodiments, a disease such as a concussion is detected second eye test shows a change in morphology of a structure of the eye as compared to the morphology of the structure of the eye shown in the first eye test. In particular embodiments, the structure of the eye is selected from the group consisting of the blood vessels in the retina, the retina, the iris, and the pupil. In particular embodiments, the structure is the central retinal artery and/or choroidal blood vessels.

In certain embodiments, the methods further comprise storing the first and second images of the first and second eye tests of the subject in a storage medium. In some embodiments, the second eye test is administered after the subject has performed physical activity. In other embodiments, the second eye test is administered after the subject has sustained contact to the head. In still other embodiments, the second image is obtained within 30 minutes of the subject receiving a head trauma.

In particular embodiments, the methods further comprise storing the second image (such as a still image of the eye, a series of still images of the eye and/or a moving visual image of the eye) of the second eye test of the subject in a storage medium. In certain embodiments, a disease is detected when the diameter of a blood vessel is altered in the second eye test as compared to the diameter of the blood vessel in the first eye test. In some embodiments, the diameter of the blood vessel is altered by at least 10% between the first and second eye tests. In other embodiments, the diameter of the blood vessel is altered by at least 5% between the first and second eye tests.

In particular embodiments, a disease is detected when the diameter of the blood vessel is smaller in the second eye test as compared to the diameter of the blood vessel in the first eye test. In more particular embodiments, a disease is detected when the diameter of the blood vessel is greater in the second eye test as compared to the diameter of the blood vessel in the first eye test. In other embodiments, a disease is detected when a second dilation of a pupil shown in the second image is altered when compared to a first dilation of the pupil shown in the first image. In still other embodiments, the diameter of the pupil is altered by at least 5% or alternatively at least 10% as shown in the second eye test as compared to the diameter of the pupil in the first eye test.

Another aspect disclosed herein relates to systems comprising a recording device configured to record a first image of a first eye movement test of a subject and a second image of a second eye movement test of the subject and a display. The systems further comprise at least one processor and a communication link connecting the recording device and the display to at least one processor and a memory. The systems also include the memory providing code to the at least one processor. The at least one processor controls an interface to receive the first and the second images from the recording device and store the first image in a storage medium. The at least one processor also controls the interface to compare the first and second eye tests shown in the first and second images, respectively. The at least one processor also controls the interface to calculate an alteration in eye movement or the morphology of the eye based on differences between the first image showing the first eye test and the second image showing the second eye test. The at least one processor also controls the interface to transmit the calculation results to the display.

In certain embodiments, the first image is a still image of the eye. In particular embodiments, the first image of the first eye movement test is a series of still images of the eye. In other embodiments, the first image is a moving visual image of the eye. In certain embodiments, the second image is a still image of a structure of the eye. In particular embodiments, the second image is a series of still images of the eye showing movement of the eye or alternatively a structure of the eye. In other embodiments, the second image is a moving visual image of the eye.

In certain embodiments, the at least one processor controls the interface to retrieve the first and second images from the storage medium. In certain other embodiments, the at least one processor controls the interface to store the second image in the storage medium.

In some embodiments, the first and second eye tests show a movement of the eye. In particular embodiments, the first and second eye tests each show a lateral eye movement. In other particular embodiments, the system calculates a change in speed between a first lateral eye movement shown in the first moving visual image and a second lateral eye movement shown in the second moving visual image. In still other embodiments, the first and second eye movements are each a vertical eye movement. In yet other embodiments, the system calculates a change in speed between a first vertical eye movement shown in the first moving visual image and a second vertical eye movement shown in the second moving visual image. In certain embodiments, the first and second eye movements are each a dilation of a pupil. In particular embodiments, the system calculates a change in a second dilation of a pupil shown in the second moving visual image compared to a first dilation of the pupil shown in the first moving visual image.

In certain embodiments, the first and second eye tests show a structure of the eye. In particular embodiments, the first and second eye tests each show the structure of the eye, which is selected from the group consisting of the blood vessels in the retina, the retina, the iris, and the pupil. In particular embodiments, the structure is the central retinal artery and/or choroidal blood vessels.

In more particular embodiments, the at least one processor controls the interface to calculate a difference in morphology of a structure between the first and second images. In even more particular embodiments, the at least one processor controls the interface to determine whether the diameter of a blood vessel shown in the second image has changed by at least 10% (or alternatively by at least 5%) as compared to the diameter of the blood vessel as shown in the first image. In certain embodiments, the at least one processor controls the interface to calculate a difference in pupil dilation between a first eye test and a second eye test based on the first and second images, respectively. In other embodiments, the at least one processor controls the interface to calculate a difference in pupil dilation of at least 10% (or alternatively at least 5%) between a first eye test and a second eye test based on the first and second images, respectively.

BRIEF DESCRIPTION OF THE FIGURES

The foregoing and other objects of the disclosed processes and systems, the various features thereof, may be more fully understood from the following description, when read together with the accompanying drawings in which.

DETAILED DESCRIPTION

Figure 1:
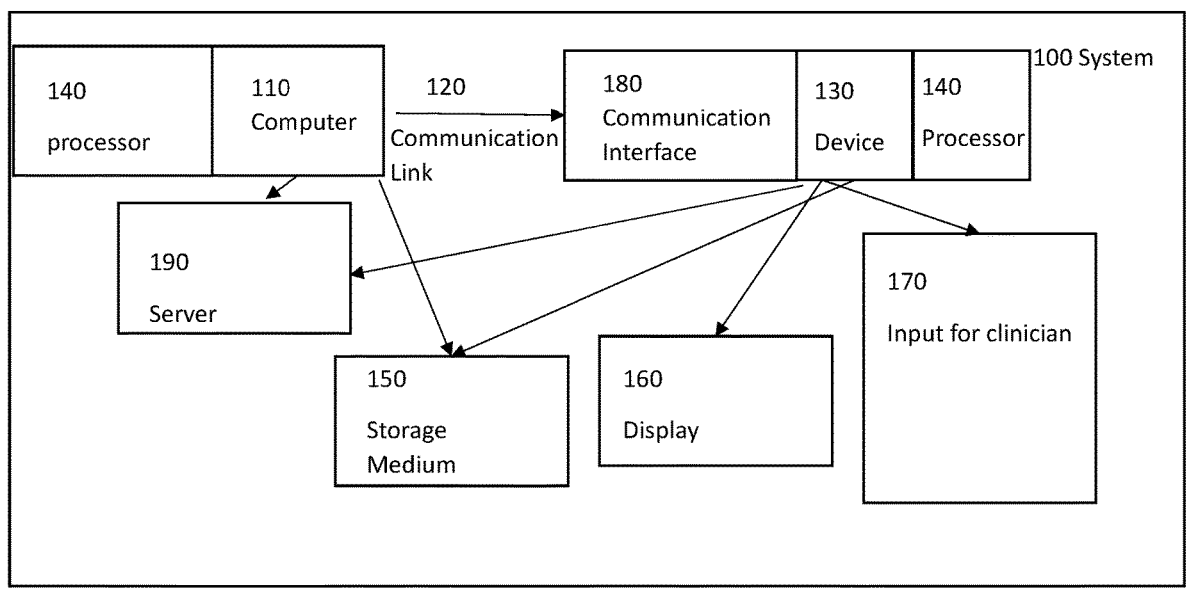
FIG. 1 is a schematic representation of an embodiment of the systems disclosed herein.

The patent and scientific literature referred to herein establishes knowledge that is available to those of skill in the art. The issued U.S. patents, allowed applications, published foreign applications, and references, including GenBank database sequences, that are cited herein are hereby incorporated by reference to the same extent as if each was specifically and individually indicated to be incorporated by reference.

1. Methods of Detecting Disease

Disclosed herein are methods of detecting a disease associated with alterations in brain metabolism. The disclosed methods rely, in part, on detecting changes in eye function caused by perturbations in metabolism caused by a disease. For instance, the brain's mechanisms to recover from a traumatic event, such as a contact with the head, involve changes in glucose and/or oxygen levels. Immediately after the traumatic event, there is an abrupt, indiscriminant release of neurotransmitters along with unchecked ionic fluxes (Giza and Hovda, (2001) *J. Athl. Train.* 36(3): 228-235). In addition to these changes in brain function, the brain suffers an alteration in glucose metabolism (id.). This alteration in glucose metabolism is caused by the sodium-potassium pumps increasing workload (id.).

During this period of increased glucose metabolism, cerebral blood flow diminishes, triggering a radical decrease in cellular energy (id.). The brain thus goes into a period of depressed metabolism, which leads to changes in neurotransmission and alterations in physiological markers such as eye movement (see Trayford. *Concussion—Look To The Eyes*, world wide web at cfneurology.com).

Other diseases can cause alterations in oxygen and/or glucose levels in the brain or mimic such a condition. A stroke reduces the levels of oxygen and glucose to at least one part of the brain. Such reduction in these levels of oxygen to the brain can lead to brain damage and alterations in function (Philip Cryer. (2007) *J Clin Invest.* 117(4):868-870). A concussion can also lead to localized or generalized perturbations of glucose and/or oxygen levels in the brain. Additionally, diabetes type 1 and type 2 lead to deprivation in glucose to tissues and can cause significant alterations in brain function. These alterations in brain function are manifested in the functionality of other structures controlled by the brain such as the eye.

Eye muscles control movements of the eye. The muscles are controlled by cranial nerves (for example, cranial nerves III, IV, and VI). Furthermore, the oculomotor nerve controls the pupil. These nerves are directly connected to structures of the brain (e.g., the midbrain (cranial nerves III and IV), the pons (cranial nerves V through VIII), and the medulla oblongata (cranial nerves IX through XII)). Accordingly, eye movements are sensitive to perturbations of brain metabolism.

Oculomotor functions consist of extraocular muscle function and intrinsic ocular muscles (controlling the lens and pupil). When the eye moves, certain muscles increase eye movements while other muscles decrease it. Eye movements include: adduction (the pupil directing toward the nose); abduction (the pupil directed laterally); elevation (the pupil directed up); depression (the pupil directed down); intorsion (the top of the eye moving toward the nose); and extorsion (the superior aspect of the eye moving away from the nose). There are also simple horizontal eye movements. For example, moving the pupil laterally involves the lateral rectus. Medial movement of the pupil involves the medial rectus muscle. Regarding the iris, this structure receives both sympathetic and parasympathetic nerves. These nerves innervate the pupillary dilator muscles and sphincter muscles. These muscles control pupil dilation.

In particular embodiments, the disclosed methods detect a disease. Examples of such diseases include Alzheimer's Disease, hepatitis, diabetes type 1 and type 2, diseases of the kidney, insulinoma, nesidioblastosis, Addison's disease, under-active pituitary gland, mild traumatic brain injury such as concussion, liver disease, diseases associated with hyperglycemia include diabetes type 1 and type 2, stroke, myocardial infarction, dysfunction of the thyroid, dysfunction of the adrenal or pituitary gland, pancreatic cancer, infections, encephalitis, brain tumors, meningitis, as well as issues caused by medications such as corticosteroids, octreotide, beta blockers, epinephrine, thiazide diuretics, niacin, pentamidine, protease inhibitors, and L-asparaginase.

In certain embodiments, a concussion causes a disease. As used herein, the term "concussion" means a traumatic brain injury that results in one or more symptoms including headache, cognitive deficits, emotional changes, loss of sleep, loss of consciousness, irritability, reaction time, and changes in eye reactions. The disclosed methods can detect a change in eye movement or the morphology of the eye in a subject that has suffered a concussion as compared to the subject's normal eye movement or eye morphology. In certain embodiments, the normal eye movement or eye morphology is determined by a baseline test of the subject. The baseline test identifies the subject's normal eye function and morphology. The baseline test can be compared to a second test of the subject, the second test identifying a present eye function or eye morphology of the subject. Changes between the baseline test and the second test are indicative of a disease.

The methodologies disclosed herein can comprise a first determination of a subject's normal eye movement or morphology of a structure of an eye. Exemplary structures of the eye include the blood vessels in the retina (e.g., the central retinal artery and/or choroidal blood vessels), the retina, the iris, and the pupil. This determination is the baseline eye movement or structure of the eye for the subject. In some embodiments, a first eye movement or morphology test is administered to the subject. The first eye movement or eye morphology test can be an eye test of a subject in a normal state. In certain embodiments, the first eye test determines eye movement speed of a subject, such as the speed of the lateral, vertical and diagonal eye movement of a subject's eyes. Furthermore, extraocular movement tests can determine the saccades of the eyes (i.e., the ability of the eyes to fixate rapidly from one object to another) and optokinetic nystagmus of the eyes (see world wide web at neuroexam.com). In particular embodiments, the eye movement test is a King-Devick Test (Galetta et al. (2011) *Neurology* 76(17): 1456-1462).

In other embodiments, the first eye test determines a morphology of a structure of the eye. In particular embodiments, the test identifies a diameter in a blood vessel. The blood vessel can be located in any region of the eye. For instance, the blood vessel can be in the retina (e.g., central retinal blood vessel). The blood vessel can be located in the choroid. The blood vessel can be the long posterior ciliary artery, the central retinal vein, the short posterior ciliary artery, episcleral artery, the anterior ciliary artery, and the vorticose vein. In other embodiments, the structure of the eye can be the iris and/or the pupil. The diameter of the iris or the diameter of the pupil can be determined by the first eye test.

The eye test identifying a first eye morphology can be stored on a storage medium such as DVDs, CDs, and VHS. Alternatively, the storage medium can be on a computer, a server, a memory stick, and/or a mobile device, such as a cell phone, tablet, and a notebook. Returning to the eye movement test, the disclosed methods comprise recording a moving visual image (e.g., video) of the subject's eye movements as the first eye movement test is administered to the subject. The moving visual image (i.e., a first moving visual image) can be recorded on media such as DVDs, CDs, and VHS. Alternatively, the moving visual image can be recorded and stored as a digital image in a storage medium. The storage medium can be a memory located on a device. The device can be located on a computer, a server, a memory stick, and/or a mobile device, such as a cell phone, tablet, and a notebook. Furthermore, digital formats for moving visual images are known in the art. Examples of digital formats include 3GP, animated GIF, AVI, FLV, MPEG, MPEG1, MPEG2, FLA, M4V, QuickTime, MP4, NSV, RealMedia, SVI, SWF, and WMV.

Aspects of the disclosed methods also comprise administering a second eye test to the subject. The second eye test can detect a second eye movement and/or a second morphology of the eye structure. In certain embodiments, the second eye test is the same as the first eye test administered to the subject. In other embodiments, the second eye test is recorded as a moving visual image (i.e., a second moving visual image), a still image, or a series of still images. In some embodiments, the second image of the second eye test is stored in a storage medium.

In particular embodiments, the second eye test is administered after the subject has performed physical activity. In particular embodiments, the second eye test is performed after the subject has been involved in a contact sport. In more particular embodiments, the second eye test is performed after the subject has suffered a blow to the head. Notwithstanding such embodiments, the second eye test can be administered at any time when there is a need to determine whether the subject may have suffered a traumatic head injury. For instance, the second eye test can be administered within 30 minutes of the subject receiving a head trauma. Alternatively, the second eye test can be administered about 30 minutes to about two weeks after the subject received a head trauma.

Aspects of the methods further comprise analyzing a difference between a first eye movement or the structural morphology of the eye shown in the first image and a second eye movement or the structural morphology of the eye shown in the second image and detecting a concussion when the second eye movement or structural morphology of the eye of the subject is altered compared to the first eye movement or the structural morphology of the eye of the subject. Analysis of the difference between the first eye movement or the structural morphology of the eye of the subject and the second eye movement or the structural morphology of the eye of the subject can be performed by the clinician. In such embodiments, the clinician can view the first and second images simultaneously on a display to detect a change in the speed of the eye movements or the difference in morphology of the structure of the eye during the second eye test as compared to the speed of the eye movements or the structural morphology of the eye detected during the first eye test administered to the subject in the normal state. An alteration in the speed of eye movement, such as a decrease in speed, or the morphology of the structure of the eye, such as a change in the diameter of a blood vessel, indicates that the subject suffers a disease altering the subject's glucose and/or oxygen state. In certain embodiments, the test indicates that the subject has suffered a concussion. In some embodiments, a concussion is detected when the eye movement of the subject in the second eye movement test is retarded as compared to the eye of the subject in the first eye movement test.

In other embodiments, a disease such as a concussion is detected when the morphology of a structure of the eye is altered compared to a normal state. For instance, the diameter of a blood vessel can be reduced by at least 5% (or by at least 10%) in the second eye test as compared to the first eye test. The diameter of the blood vessel can be increased by at least 5% (or by at least 10%) in the second eye test as compared to the first eye test. In some embodiments, whether the pupil is dilated during a second eye test as compared to a first eye test can be determined. In certain embodiments, a disease or a concussion is detected when a pupil is dilated in a second eye test as compared to a first eye test. In some embodiments, the width of the iris is an indicator of a disease or a concussion. In other embodiments, the width of the iris shown in the second eye test is reduced as compared to the width of the iris shown in the first eye test. In particular embodiments, the width of the iris shown in the second eye test is enlarged as compared to the width of the iris shown in the first eye test.

In some embodiments, a disease (e.g., concussion) is detected when the morphology of nerves innervating the eye are altered. In certain embodiments, the size of the nerve innervating the eye of a subject suffering from a disease is decreased as compared to the size of the nerve innervating the eye of a normal subject. In particular embodiments, the nerves are cranial nerves. In other embodiments, the nerves have alterations in other morphological characteristics such as vesicle formation, nerve axon, and nerve terminal.

In other embodiments, an alteration in the ability of the eye to track a moving object during an eye movement test is indicative of a concussion. For instance, the inability of the subject to track a rapidly moving object in the second eye movement test when the subject was able to follow the object in the first eye movement test is indicative that a brain injury has occurred. In some embodiments, an alteration in the ability of the eye to maintain focus on a particular object in the second eye movement test when the subject was able to maintain focus in the first eye movement test is indicative of a concussion. The present methodology thus identifies alterations in a subject's eye movement in a second test as compared to a first eye movement test, which identifies the normal baseline eye movement of the subject.

Aspects of the disclosed methods allow for the first and second eye tests to determine movements such as lateral eye movements, vertical eye movements, diagonal eye movements, and dilation of the pupils. In certain embodiments, the first and second eye movement tests obtain information regarding a combination of eye movements and/or the morphology of an eye structure. For instance, the eye movement tests can be used to detect a combination of lateral eye movements, vertical eye movements, diagonal eye movements, and dilation of one or more pupils.

Aspects of the methods disclosed herein also comprise storing the first and second images obtained for a subject in a storage medium of a computer or a server. The images can then be accessed by a medical professional to allow for review of the subject's performance on eye movement tests over time. Furthermore, the methods disclosed herein allow for access of the images by the internet.

The disclosed methods allow for the accumulation of information regarding the "normal" eye movements or the morphology of one or more structures of the eye of a group of subjects (e.g., a large sample of individuals). Such information would be used as a baseline, normal eye movement or normal morphology of one or more structures of an eye for subjects in which a normal baseline eye test is unavailable. In such embodiments, the first image is not performed. Rather, the clinician is provided with information relating to what the normal eye movement or the normal morphology of a structure of an eye of the subject should be, depending on the subject's gender, age, and other factors. Thus, when the clinician desires to determine the normal eye movement or eye morphology for an individual, the clinician inputs the subject's age, gender, and other factors into a computer or other device prior to testing the subject. The clinician is then provided from a database with the normal eye movement or normal eye morphology for the particular subject. This information is then compared to the eye movement test administered to the subject. In these embodiments, the second eye test is the only eye test administered to the subject and the second image is the only image obtained.

Aspects of the methods disclosed herein can also allow for recording of iris structure and size. In certain embodiments, the structure or size of the iris is scanned. The scan is then compared to another recording that is retrieved from a prior recording stored in a computer-readable medium. The prior recording can be a baseline reading of a subject or a prior recording. The comparison can identify eye dysfunctions by assessing and calculating changes in pupil response to a stimulus such as a three-dimensional object, iris structure, changes in dominant eye, and visual acuity.

The methods disclosed herein also detect changes in eye reflexes such as pupillary light reflex, corneal reflex, and vestibulo-ocular reflex. The methods disclosed herein can detect alterations in eye reflex through eye tests utilizing light shined into the subject's eyes and the recording of the response of structures of the eyes.

The methods disclosed herein can also be used to record the ability of the lens to thicken or thin to maintain focus on an image moving toward the eye. In some embodiments, a three-dimensional object is moved toward the eye and the response of the lens to the movement of the object is recorded and compared to a baseline recording.

In other aspects, the methods disclosed herein can detect changes in the ability of the eyes to converge on an object moving toward the midline between the eyes. In some embodiments, a three-dimensional object is positioned between the eyes of a subject and moved toward the midline. The tracking behavior of the eyes is recorded and the images are compared to baseline images.

Aspects of the methods disclosed herein can be used to detect changes in a subject's visual fixation on an object. In certain embodiments, the subject turns her head in the direction of an object that is moved. In some embodiments, the methods detect the differences in fine movements of the eyes in tracking the object as compared to baseline recordings.

Aspects of the methods disclosed herein can be used to detect changes in a subject's pupil to dilate in response to a pinch or stimulus on the neck or cheek of the subject. In certain embodiments, a stimulus is provided to the neck or check of the subject and the dilation of the ipsilateral pupil is measured. The measurements can then be compared to a baseline recording of the subject.

Aspects of the methods disclosed herein can be used to detect changes in the eyes of a subject to react to a sound. In certain embodiments, a sound is made to one side of the head of a subject. The movement of the eyes to identify the sound is recorded and the recording is compared to a baseline of the subject.

It should be noted that the baseline measurement of a subject does not imply that there is only one set of recordings for a particular subject. For instance, the subject may have been tested on several occasions. When a subject's eye structure, movement, or function is measured, then the recordings of the images can be compared to any previous recording of the subject. As such, a subject's eye test can be compared to the next most recent test in the database to determine the change in a subject's eye structure, movement, or function over a short period of time. In embodiments where a subject has been tested multiple times, then the change in eye structure, function, or movement over time can be measured and determined.

Additionally, it should be noted that the use of the term "first set of images," "first one or more images," "first image," "second set of images," "second one or more images," or "second image" should not be construed to mean that only two sets of images or two images have been taken of the subject. A subject could have a nearly unlimited number of eye tests stored on the system and the use of terms such as "first" or "second" are used only to differentiate between images that are being compared using the disclosed systems and methods.

2. Systems

Disclosed herein are also systems useful for the rapid and objective determination of concussions. An embodiment of the systems disclosed herein is shown in FIG. 1. Referring now to FIG. 1, an exemplary system 100 includes a computer 110. Computer 110 includes a communication link 120, such as a bus, connected to a device 130. The communication link 120 provides two-way data communications between the computer 110 and the device 130. The communication link 120 can be a local area network (LAN). The communication link 120 can be hard-wired and/or wireless.

The communication link 120 connects the computer 110 and device 130 through a communication interface 180. For example, one or more devices 130 may be networked together and to one or more computers 110 to form a network of devices.

Returning to the device, the device 130 is capable of taking images such as moving visual images, still images, and/or a series of still images of the eyes of a subject during an eye test. The device can also be a portable device (Volk Optical, Inc., Mentor, Ohio). Examples of other devices having image capability include retinal imaging devices produced by Optos North America (Marlborough, Mass.), mobile devices such as tablets, and video recording devices. The device 130 and computer 110 both comprise a processor 140 for executing the software stored in the memory of the device 130 and/or computer 110. Furthermore, the device 130 and/or computer 110 have code that allows the device 130 and/or computer 110 to analyze differences between two or more images showing the movement of the eyes of a subject or a structure of the eye of a subject. The computer 110 also includes a memory for storing information (e.g., the images obtained by the device 130) and instructions to be executed by processor 140. The memory also stores intermediate information during execution of instructions by processor 140. The system 100 further includes a storage medium 150 such as a CDROM, DVD, or other static storage, such as a hard drive or solid state storage device.

The system 100 also includes a display 160, such as a liquid crystal display (LCD), for displaying information to a clinician or other medical personnel. The display 160 allows the clinician to view the images stored on the memory of the device 130 or the computer 110. Furthermore, the images may be stored on a storage medium (not shown). An input 170 can be connected to the device 130 to allow the clinician to change more easily the views of the images and to compare two or more images side-by-side. The input 170 can be a mouse, a trackball, or other controller.

Information from the device 130 and/or computer 110 can be transmitted across a network. In such embodiments, the computer 110 and/or device 130 are connected to a server 190 (which may store images for processing) and/or to data equipment operated by an Internet Service Provider (ISP).

The processor 140 controls an interface to receive the first and the second images from the device 130 and store a first set of images in a storage medium (not shown). The processor 140 controls the interface to retrieve the first and second sets of images from the storage medium. The processor 140 also controls the interface to compare the first and second eye movements or functions shown in the first and second sets of images, respectively. The processor 140 also controls the interface to calculate an alteration in eye movement based on differences between a first eye test and a second eye test. The processor 140 also controls the interface to calculate an alteration in the morphology of a structure of the eye based on differences between the structure shown in a first image or a plurality of images and the structure shown in a second image or a plurality of images. The processor 140 further controls the interface to transmit the calculation results to the display 160. Furthermore, the processor 140 controls the interface to store the second set of images in the storage medium.

Aspects of the systems disclosed herein can include software to assess images taken of pupil and iris dimensions. The systems disclosed herein can include software to assess eye movement and structures of the eye such as retinal veins and arteries. In certain embodiments, the systems include software to account for head movement and to eliminate the effects of such movement from the calculations of differences between a baseline test of a subject and a second test of a subject. Such software is known in the art and can be found in systems provided by Micromedical Technologies Inc. (Chatham, Ill.). Additionally, eye tracking software can be purchased commercially from SensoMotoric Instruments GmbH (Teltow, Germany).

In additional embodiments, the systems comprise a portable headpiece to hold the subject's head in place. The headpiece can also comprise light-blocking flaps to block light from affecting the examination of the subject. The headpiece is also adjustable and comprises padding to ensure the comfort of the subject. In particular embodiments, the headpiece comprises flaps that can be moved over each eye to block each eye during an eye test. The headpiece can further comprise connections to a support such as a table or other solid flat structure so as to reduce movement of the subject's head.

In some embodiments, the systems comprise a viewing screen that the subject views. The screen is capable of showing one or more objects—stationary or moving—to the subject. In other embodiments, the viewing screen is connected to a computer that allows a clinician or other evaluator to control the objects shown on the screen. In particular embodiments, the screen allows for objects or other stimuli to come from outside the visual field from any direction.

Figure 2:
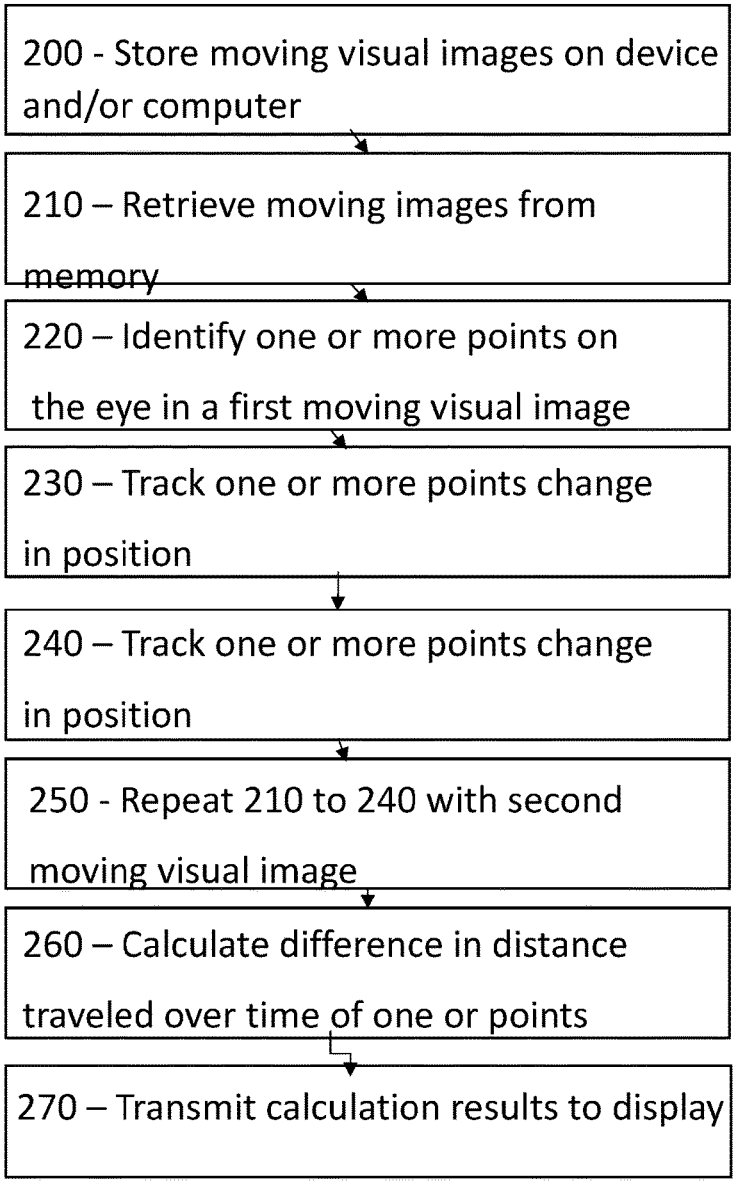
FIG. 2 is a schematic representation of one embodiment of the functioning of the systems disclosed herein.

FIG. 2 is a schematic representation of the steps that the disclosed systems can take to calculate an alteration in eye movement or morphology of an eye structure based on differences between a first eye movement or morphology of an eye structure shown in the first image and a second eye movement shown in the second image. A first image is stored in memory from a prior eye test, the prior eye test being a baseline test. The second image is recorded by a device connected to the system. The device stores the second image in memory on the device and at a computer connected to the device (200). The computer is then instructed to retrieve the first and second images from memory (210).

Once the images have been retrieved, the device performs a comparison of the first and second images. This comparison involves identifying one or more points of the eye in the first image and identifying the same one or more points of the eye in the second image (220). It should be recognized that a point can be a single pixel or a group of pixels that contact one another.

In this illustrative embodiment, the system uses non-contact, optical measurement of the eye movement or the morphology of a structure of the eye. Light, such as infrared light, is reflected from the eye and sensed by a video camera or some other specially designed optical sensor. For eye movement, the information is then analyzed to extract eye rotation from changes in reflections as the eye moves. Video based eye trackers use the corneal reflection (the first Purkinje image) and the center of the pupil as features to track over time. These features represent the one or more points in the tracked in the moving images. In certain instances, the system uses dual-Purkinje eye tracker, which utilizes reflections from the front of the cornea (first Purkinje image) and the back of the lens (fourth Purkinje image) as features to track.

For studies of eye morphology, still images or series of still images can be used to identify a structure in the eye. Tests of eye structures are known in the art and include fluorescein angiography (Kumar, Vinay. *Eye, Retina and Vitreous, Retinal Vascular Disease. Robbins Basic Pathology* (8th ed.). Philadelphia: Saunders/Elsevier (2007), Ch. 29).

Returning to FIG. 2, the system measures the alteration in movement speed of the subject's eyes or alterations in the morphology of one or more structures of the eye between the first and second eye tests as shown in the first and second images after comparing the first and second images. The measurement is made by tracking one or more points on the eye of the subject in the first image as they move in response to a stimuli (230). For eye movement, the system then determines the distance traveled of each of the one or more points in the first moving visual image by determining the change in position in the x- and y-axes in a given period of time (240). This amounts to a change in position of the one or more points. In certain embodiments, the system will account for the change in position of each point that is identified independently. In other embodiments, the system identifies the pupil of the subject. This identification is accomplished by identifying the pixels that make up the pupil and regarding each pixel as a point. The change in position of each point during an eye movement test is calculated as noted above in the discussion of FIG. 2. For the morphology of a structure of the eye, the system determines the alteration in size or shape of the structure in a second image as compared to the size or shape of the structure in a first image.

Following the same procedure for the second image, the system identifies the same points on the eye of the subject and calculates the speed of movement or the alteration in size or shape of a structure of the eye by comparing one or more points in the second image with one or more points in the first image (250). Once the determination of distance traveled over time is made in the first and second images, the system calculates the difference in speed between the first and second images or the change in size or shape between the first and second images (260). The system then transmits the information to the display (270).

The system can also calculate the distance traveled for one or more points without calculating the speed of the points in the moving visual images. In such embodiments, the system determines whether any movement occurred in either image and determines the difference in movement between the images. For instance, the ability of the pupil to adjust to light intensity can be determined by noting points along the edge of the pupil and determining the distance traveled by the points in a pupil dilation test.

Furthermore, the system allows clinicians to identify one or more points for the system to calculate the change in speed or position of the points between eye movement tests. The system also allows for the clinician to identify one or more structures for analysis. In certain embodiments, the clinician will choose points that identify structures such as veins, arteries, pupils, or other gross physical structures. For example, the clinician uses a mouse to select one or more points on, or structures of, the eye of the subject as shown in the images. The clinician can then instruct the system to calculate the change in speed or position of the points, or the change in size or shape of a structure, shown between the first and second tests.

In certain embodiments, the system further normalizes images taken over time. Images are taken at different times, in different lighting conditions, using potentially different equipment, and in different patient states. Normalization is performed by the system automatically when two images are compared. One method of normalization includes first estimating a background image and then subtracting the estimated background image from the original (e.g., by low pass filtering the original image). The normalized images may be stored or used immediately by the system.

We claim:

1. A method of detecting an alteration in glucose metabolism in the brain of a subject, the method comprising:
   a. administering a first eye test to the subject when the subject is in a normal state;
   b. obtaining a first set of one or more images of the first eye test of the subject;
   c. administering a second eye test to the subject;
   d. obtaining a second set of one or more images of the second eye test of the subject;
   e. identifying one or more differences between the first set of one or more images and the second set of one or more images; and
   f. detecting the alteration in glucose metabolism when the second eye test shows an alteration in either a movement or a function of an eye of the subject based on the one or more differences identified between the first set of one or more images and the second set of one or more images.

2. The method of claim 1, wherein the alteration in glucose metabolism is detected when an eye movement of the subject identified in the second test is retarded as compared to an eye movement of the subject identified in the first eye test.

3. The method of claim 1, wherein the first and the second eye tests are each a King-Devick Test.

4. The method of claim 1 further comprising storing the first one or more images of the first eye test of the subject in a storage medium.

5. The method of claim 1, wherein the second eye test is administered after the subject has performed physical activity.

6. The method of claim 1, wherein the second eye test is administered after the subject has sustained contact to the head.

7. The method of claim 1, wherein the second one or more images is obtained within 30 minutes of the subject receiving a head trauma.

8. The method of claim 1 further comprising storing the second one or more images of the second eye test of the subject in a storage medium.

9. The method of claim 1, wherein a first and a second eye movement are selected from the groups consisting of lateral eye movements, vertical eye movements, diagonal eye movements, dilation of a pupil, and combinations thereof.

10. The method of claim 9, wherein the alteration in glucose metabolism is detected when a second dilation of a pupil shown in the second one or more images is altered when compared to a first dilation of the pupil shown in the first one or more images.

11. The method of claim 9, wherein the alteration in glucose metabolism is detected when a second lateral eye movement shown in the second one or more images is altered when compared to a first lateral eye movement shown in the first one or more images.

12. The method of claim 9, wherein the alteration in glucose metabolism is detected when a second vertical eye movement shown in the second one or more images is altered when compared to a first vertical eye movement test shown in the first one or more images.

13. The method of claim 1, wherein the first one or more images is a visual moving image.

14. The method of claim 1, wherein the second one or more images is a visual moving image.

15. The method of claim 1, wherein the alteration in glucose metabolism comprises insulin-resistance.

16. The method of claim 1, wherein the detection of the alteration in glucose metabolism detects a cognitive disease.

17. The method of claim 1, wherein the detection of the alteration in glucose metabolism detects diabetes mellitus I or II.

18. The method of claim 1 further comprising accessing the first set of one or more images from a computer-readable storage medium.

19. The method of claim 18, wherein the computer-readable storage medium is accessed over a network from a remote location.

20. The method of claim 1 further comprising comparing the first set of one or more images to the second set of one or more images.

* * * * *